United States Patent [19]

Kuehn

[11] 4,159,376

[45] Jun. 26, 1979

[54] ISOCYANURATES FROM UNSATURATED MONOHYDRIC ALCOHOLS AND POLYISOCYANATES

[75] Inventor: Erich Kuehn, Wilmington, Del.

[73] Assignee: ICI Americas Inc., Wilmington, Del.

[21] Appl. No.: 819,239

[22] Filed: Jul. 27, 1977

[51] Int. Cl.² ............................................. C07D 251/34
[52] U.S. Cl. ...................................... 544/222; 526/261
[58] Field of Search .......................................... 544/222

[56] References Cited

U.S. PATENT DOCUMENTS

| 2,952,665 | 9/1960 | Bunge et al. | 544/222 |
| 3,121,082 | 2/1964 | Guttag | 544/214 |
| 3,737,432 | 6/1973 | George et al. | 544/222 |
| 3,763,269 | 10/1973 | Formaini | 260/74 UA |

Primary Examiner—John M. Ford

[57] ABSTRACT

Isocyanurate polymers having improved physical properties are disclosed. Unsaturated isocyanates are prepared by reacting a polyisocyanate with a monohydric alcohol containing a vinylidene group to form an isocyanate-containing urethane and then reacting the isocyanate-containing urethane with tris(2-hydroxyethyl)isocyanurate to form an unsaturated isocyanurate. The unsaturated isocyanurate may be homopolymerized or copolymerized with ethylenically unsaturated compounds to form isocyanurate polymers having an excellent combination of physical properties.

11 Claims, No Drawings

ISOCYANURATES FROM UNSATURATED MONOHYDRIC ALCOHOLS AND POLYISOCYANATES

The present invention relates to isocyanurates and to methods of preparing said isocyanurates. More particularly, this invention relates to the preparation of ethylenically unsaturated isocyanurates by reacting a polyisocyanate with a monohydric alcohol containing a vinylidene group to form an unsaturated urethane containing one free isocyanate group and then reacting three mols of the urethane with one mol of tris(2-hydroxyethyl)isocyanurate to form an ethylenically unsaturated isocyanurate.

The expression "vinylidene group" when used in this application means the group characterized by the formula:

wherein the two free valence bonds are not both connected to the same carbon atom.

The expression "polyisocyanate" when used in this application means a compound containing two or more NCO groups.

The expression "aromatic polyisocyanate" when used in this application means a compound containing at least two isocyanate groups attached directly to a carbon atom of an aromatic ring.

The expression "isocyanurate" means a compound containing the structure:

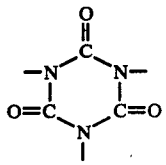

Many polyester polymers known in the art have excellent corrosion resistant properties but very poor high temperature properties. Other polymers known in the art have good elongation and high impact strength but poor corrosion resistant properties and poor high temperature properties. There is a demand in the polymer industry for polymers having an improved combination of properties.

It has been discovered in accordance with the present invention that a novel class of ethylenically unsaturated isocyanurates, which may be polymerized to yield polymers having an improved combination of properties, such as a combination of excellent hardness, good elongation, extremely high impact strength, excellent toughness and good corrosion resistance, may be prepared by a two-step process which comprises a first step of reacting a polyisocyanate with a monohydric alcohol containing a vinylidene group to form an isocyanate-containing urethane and a second step of reacting the isocyanate-containing urethane with tris(2-hydroxyethyl)isocyanurate to form an ethylenically unsaturated isocyanurate. The isocyanurate polymers retain this improved combination of improved properties when heated to elevated temperatures.

To assist in describing the invention so that it may be understood by those skilled in the art, but without wishing to be bound by any particular theory, it is believed that the two-step process of this invention may be illustrated by the following equations:

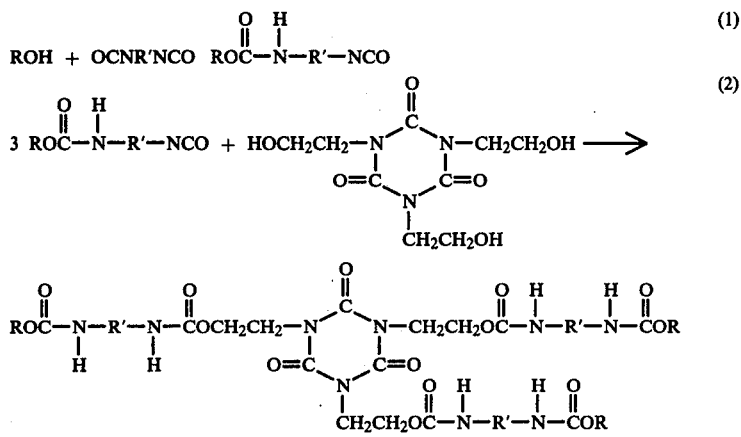

where R is a monovalent organic radical containing a vinylidene group, R' is a divalent organic radical free of a group which is reactive with isocyanate groups. If a trifunctional isocyanate is used then two moles of the monohydric alcohol are used per mole of isocyanate.

Any polyisocyanate may be used in the process of this invention. For example, the polyisocyanate may be saturated, unsaturated, aromatic, aliphatic, cycloaliphatic, monomeric or polymeric. The only requirement is that the polyisocyanate should not contain any groups which would interfere with the reaction of the isocyanate group of the polyisocyanate with the hydroxyl group of the monohydric alcohol. Illustrative examples of polyisocyanates which are particularly useful in this invention include 2,4-tolylene diisocyanate; 2,6-tolylene diisocyanate; m-phenylene diisocyanate; p-phenylene diisocyanate; 1,5-naphthalene diisocyanate; 1,6-hexamethylene diisocyanate; 4,4'-diphenyl ether diisocyanate; 4,4',4''-triphenylmethane triisocyanate; 2,4,4'-triisocyanato triphenyl; 2,4,4'-triisocyanate diphenyl methane; 2,4,6-triisocyanato diphenyl ether; 2,2',4-triisocyanate diphenyl ether; 2,2',4-triisocyanate diphenyl sulfide; 2,4,4'-triisocyanato diphenyl sulfide; 2,3',4-triisocyanato-4'-methyl diphenyl ether; 2,3',4-triisocyanato-4'-methoxy diphenyl ether; 2,4,4'-triisocyanato-3'-chlorodiphenylether; 4,4',6-diphenyl triisocyanato; 1,10-decamethylene diisocyanate; cumene-2,4-diisocyanate; 4-methoxy-1,3-phenylene diisocyanate; 4-chloro-1,3-phenylene diisocyanate; 4-bromo-1,3-phenylene diisocyanate; 4-ethoxy-1,3-phenylene diisocyanate; 2,4'-diisocyanato diphenyl ether; 5,6-dimethyl-1,3-phenylene diisocyanate; benzidine diisocyanate; 9,10-anthraceine diisocyanate; 4,6-dimethyl-1,3-phenylene diisocyanate; 4,4'-diisocyanatodibenzyl; 3,3'-dimethyl-4,4'-diisocyanato diphenyl methane; 2,6-dimethyl-4,4'-diisocyanato diphenyl; 2,4-diisocyanato stilbene; 3,3'-dimethyl-4,4'-diisocyanato diphenyl; 3,3'-dimethoxy-4,4'-diisocyanato diphenyl; 1,4-anthracene diisocyanate; 2,6-fluorene diisocyanate; 1,8-naphthalene diisocyanate; 2,6-diisocyanato benzofuran, 2,4,6-tolylene triisocyanate; 2,4,4'-triisocyanato diphenyl ether; diphenylmethane polyisocyanate available under the trademark Mondur MR having a functionality of 2.6; and 1,3-xylene-4,6-diisocyanate. A preferred class of polyisocyanates is the aromatic polyisocyanates. Preferred polyisocyanates are 2,4-tolylene diisocyanate; 2,6-tolylene diisocyanate; commercial tolylene diisocyanate (a mixture of 80% of the 2,4-isomer and 20% of the 2,6-isomer); methylene bis (p-phenylisocyanate); 1,3-cyclopentylene diisocyanate; 2,4,6-toluene triisocyanate; p-xylylene diisocyanate; tetramethylene diisocyanate; hexamethylene diisocyanate; 2,2,4-trimethylhexamethylene diisocyanate; 2,4,4'-trimethylhexamethylene diisocyanate; 3-isocyanatomethyl-3,5,5-trimethyl cyclohexyl diisocyanate; bis(2-isocyanatoethyl carbonate); isocyanate terminated prepolymers of diols and triols; and isocyanate terminated prepolymers of polyesters. A preferred class of polyisocyanates is the aromatic polyisocyanates. Preferred polyisocyanates are 2,4-tolylene diisocyanate; 2,6-tolylene diisocyanate; and mixtures thereof.

The monohydric alcohols which are useful in the process of this invention include any monohydric alcohol containing a vinylidene group and which is free of groups, other than the hydroxyl group, which are reactive with isocyanate groups. A preferred class of monohydric alcohols are prepared by reacting a monocarboxylic acid containing a vinylidene group with a dihydric alcohol. Illustrative examples of such acids include acrylic acid; methacrylic acid; ethacrylic acid; 9,12-octadecadienoic acid; 9,12,15-octadecatrienoic acid; 9,11,13-octadecatrienoic acid; and 4-keto-9,11,13-octacecatrienoic acid. Illustrative examples of dihydric alcohols include ethyleneglycol; propyleneglycol; diethyleneglycol; dipropyleneglycol; 1,3-butyleneglycol; 1,4-butyleneglycol; 2,3-butyleneglycol; pentamethyleneglycol; hexamethyleneglycol; neopentylglycol; dibromoneopentylglycol; dimethylhexenediol; dimethylhexanediol; 2-butene-1,4-diol; 2-butane-1,4-diol; 2,3-dibromo-2-butene-1,4-diol; 2,2,3,3-tetrachloro-1,4-butanediol; 2,2,4-trimethyl-1,6-hexanediol; 2,5-dimethyl-2,5-hexanediol; 2,2,4,4-tetramethyl-1,3-cyclobutanediol; 1,4-cyclohexanediol; 1,4-cyclohexanedimethanol; hydrogenated bisphenol A; and ethylene oxide and/or propylene oxide ethers of the above-mentioned diols. A preferred group of monohydric alcohols which are useful in the process of this invention comprises hydroxypropyl methacrylate; hydroxyethyl methacrylate; hydroxyethyl acrylate; and hydroxypropyl acrylate.

The tris(2-hydroxyethyl)isocyanurate used in this invention may be obtained commercially or prepared by a process described in U.S. Pat. No. 3,088,984 or in Canadian Pat. No. 960,671.

The reaction of the polyisocyanate with the monohydric alcohol, in the first step of the process, may be conducted according to reaction conditions conventional in the art for reacting an alcohol with an isocyanate to form a urethane. The only important consideration is that the relative amounts of monohydric alcohol and polyisocyanate are chosen so that the urethane formed will contain a free isocyanate group. Thus, one mole of the monohydric alcohol will be reacted with one mole of a diisocyanate and two moles of the alcohol will be reacted with one mole of a triisocyanate.

The mere mixing of the monohydric alcohol and polyisocyanate presents an exothermic reaction which in many instances generates sufficient heat for completion of the reaction. The reactants are maintained at an elevated temperature above ambient room temperature until the isocyanate content of the mixture is reduced to the point to indicate that the resulting urethane product contains one free isocyanate group per urethane molecule. In general it is preferred to conduct the reaction of the monohydric alcohol with the polyisocyanate at temperatures between 25° C. and 110° C., and preferably from about 40° C. to about 95° C. Although a catalyst is not required in this reaction, the reaction may be carried out in the presence of catalysts which promote the reaction of isocyanate groups with hydroxyl groups, for example in the presence of a cupric salt, such as cupric acetate, as taught in British Pat. No. 629,015, the disclosure of which is hereby incorporated by reference.

The monoisocyanate-containing urethane formed in step 1 may be reacted with tris(2-hydroxyethyl) isocyanurate under the same reaction conditions which may be employed in the first step. The only important consideration here is that three mols of the monoisocyanate-containing urethane prepared in the first step are reacted with one mol of the tris(2-hydroxyethyl) isocyanurate to form an isocyanurate containing three vinylidene groups.

Where the starting monohydric alcohol and/or polyisocyanate is a solid, it may be desirable to utilize an inert solvent in the reaction mixture in either the first or second step or in both steps. Illustrative examples of such suitable inert solvents include benzene, tolylene, and xylene.

Where the ethylenically unsaturated isocyanurate product is to be blended with another ethylenically unsaturated compound for use as a copolymerizable mixture, it may be desirable to utilize the unsaturated compound as a solvent for the reaction system in which the unsaturated isocyanurate product of this invention is formed. The solvent should be non-reactive, that is, the solvent should not contain any groups which would react with the isocyanate groups or in any way interfere with the urethane formation reactions in the first or second step of the process. Thus, the solvent should not contain any hydroxyl, carboxyl, or amine groups which might interfere with these reactions. This limits the suitable solvents to esters, ethers, hydrocarbons and similar solvents containing non-reactive groups. Illustrative examples of solvents which may be employed in the first and second step of the process of this invention include: styrene, methylmethacrylate, divinylbenzene, ethylmethacrylate, ethylacrylate, methylacrylate, 2-ethylhexylacrylate, 2-ethylhexylmethacrylate, butylacrylate, butylmethacrylate, cyclohexylmethacrylate, cyclohexylacrylate, t-butyl styrene, chlorostyrene, acrylonitrile, vinylidene chloride, vinyl acetate, vinyl toluene, tetrahydrofurfuryl methacrylate, vinyl pyrrolidone, diethyleneglycoldiacrylate, triethylene-glycoldiacrylate, allylmethacrylate, diallylfurmate, 1,3-butyleneglycoldimethacrylate, and polyethylene glycol diacrylate. Mixtures of solvents may also be used. A preferred solvent is styrene.

The amount of solvent employed in the process of this invention may vary over a rather wide range. The particular amount of solvent used will depend somewhat, of course, on the nature of the solvent and on the solubility of the reactants used. The amount of solvent will also depend, in the case of those solvents containing polymerizable double bonds, on the nature of the properties desired in the final product. Thus, if one is interested in preparing the ethylenically unsaturated isocyanurate of tolylene diisocyanate, hydroxypropylmethacrylate, and tris (2-hydroxyethyl)isocyanurate in styrene solvent, for example, the high temperature properties of the final product will increase as the concentration of the styrene decreases. In general, however, the amount of solvent used in the first step of the process will be chosen so that the ratio of the combined weight of monohydric alcohol and polyisocyanate to weight of solvent is from 0.33 to 9.00 and the amount of solvent used in the reaction of the monoisocyanate-containing urethane with the tris(2-hydroxyethyl)isocyanurate will be chosen that the ratio of the combined weight of the monoisocyanate-containing urethane and the tris(2-hydroxyethyl)isocyanurate to weight of solvent is from 0.33 to 2.33.

The ethylenically unsaturated isocyanurate product of this invention may be homopolymerized or copolymerized with other ethylenically unsaturated compounds. In order to accomplish such polymerization within a reasonable time, a suitable reaction initiator, of the kind frequently referred to as "free radical catalysts," may be used to promote the polymerization reaction. Exemplary of such initiators are organic peroxides such as methyl ethyl ketone peroxide, benzoyl peroxide, t-butyl perbenzoate, cumene hydroperoxide, and succinic peroxide; redox catalysts; and ammonium persulfate. Accelerators for the polymerization reaction may also be used. Exemplary of such accelerators are dimethyl aniline and cobalt naphthenate.

In order to avoid premature polymerization of the polymerizable materials used in the process of this invention, a small amount of a conventional polymerization inhibitor, such as phenol thiazine, hydroquinone, methylether of hydroquinone, t-butylcatechol, cupric salts, and the like may be incorporated either in the reaction mixture prior to reaction or to the finished product.

Polymers of the unsaturated isocyanurate products of the present invention have been found to be particularly useful in applications such as castings, coatings, and laminates, where it is desirable to have an improved combination of physical properties such as very high flex and tensile properties combined with excellent hardness, good elongation, and extremely high impact strength and good corrosion resistance and high temperature properties. They are useful in a variety of filament wound products such as pipes, ducts, and storage tanks and in molded products.

The isocyanurate product of this invention may contain any of the additives which are conventionally employed in polymerizable systems, for example, antioxidents, UV absorbers, dyes, pigments, catalysts, fibers, and fillers.

In order to describe the present invention so that it may be more clearly understood, the following examples are set forth. These examples are provided primarily for the purpose of illustration and any enumeration of details contained therein should not be interpreted as a limitation of the concept of the present invention. All parts and percentages are by weight unless otherwise specified.

The following materials are used in the examples:

Mondur MR refers to a polymethylene polyphenyl isocyanate having a functionality of 2.6 available from Mobay Chemical Company.

TDI refers to tolylene diisocyanate which is generally a mixture of the 2,4 and 2,6 isomers.

IPDI refers to isophoronediisocyanate.

THEIC refers to tris(2-hydroxyethyl) isocyanurate.

Castings are prepared by pouring the resin composition into a mold comprising two glass plates each of which had previously been coated with a mold-releasing agent, spaced ⅛ inch apart, and sealed together on three edges. After the composition is poured into the mold, the fourth edge is sealed and the composition is allowed to cure at room temperature for 24 hours. At the end of this time, the material is post cured by placing the mold in an oven at 100° C. for 4 hours. After cooling, the glass plates were separated and the solid casting is removed and tested.

Tensile strength is measured in accordance with A.S.T.M. Standard D-638-71a.

Flexural strength is measured in accordance with A.S.T.M. Standard D-790-71.

Elongation is measured in accordance with A.S.T.M. Standard D-638-71a.

Heat distortion temperature (HDT) is measured in accordance with A.S.T.M. Standard D-648-72.

Charpy impact is determined in accordance with A.S.T.M. Standard D-256.

EXAMPLE 1

Into a three-liter, four-neck flask equipped with stirrer, nitrogen inlet tube, thermometer, condenser, and dropping funnel, are added 256.4 grams of hydroxyethylmethacrylate, 244.4 grams of styrene, and 0.4 gram of hydroquinone. The resulting mixture is then heated to 50° C. at which time there is added 340 grams of TDI drop-wise. The TDI is added over a long period at a rate such that the temperature of the reaction mixture does not exceed 70° C. After the addition of the TDI is complete, the reaction mixture is maintained at 70° C. for 90 min. At the end of this time the isocyanate content is 9.37%. The reaction product is a clear, straw-colored liquid dissolved in styrene. The resulting solution is placed in a quart jar and stored under a nitrogen blanket. The second step of the process is the reaction of three moles of this styrene solution produced in step 1 with one mole of THEIC by the following procedure.

Into a one-liter, four-neck flask equipped with stirrer, nitrogen inlet, thermometer, and condenser is added 444.32 grams of the styrene solution produced in step 1, 100 grams styrene, 0.4 gram of tin octoate. The resulting mixture is stirred and 88.96 grams of THEIC are added. The resulting hazy mixture is then heated to about 80° C. at which temperature the mixture begins to clear, indicating that the reaction of the isocyanate group present in the product produced by step 1 is reacting with the hydroxyl groups on the THEIC. The reaction temperature is maintained in the range of 70° C. to 80° C. for three hours at which point 100 grams of styrene are added. The reaction is allowed to continue for an additional six hours at which time the free NCO content is less than 0.5%. The reaction is essentially complete. The reaction product, after standing over night, appeared to be hazy and jelly-like. 59 grams of ethylacrylate, 20 grams of styrene and 9 grams of hydroxyethylmethacrylate are added to break the strong thixotrope and a clear, stable, water white solution is obtained. The viscosity of this solution is 1922 centipoises at room temperature. To 600.0 grams of the resulting styrene solution of vinylidene urethane isocyanurate are added 3 grams of cobalt naphthenate, 1.2 grams of tertiary butylcatechol and 6.0 grams of Lupersol DDM, a 60% solution of methyl ethyl ketone peroxide in dimethyl phthalate, and the resulting composition used to prepare castings. The castings had the physical properties indicated in following Table I.

EXAMPLE 2

Into a one-liter, four-neck flask equipped with a stirrer, nitrogen inlet tube, thermometer, dropping funnel and condenser, there are added 245.9 grams of styrene, 375.7 grams IPDI, and 0.42 grams hydroquinone. The reacting mixture is heated to 50° C. and 228.4 grams of hydroxyethylmethacrylate are added over a 30-minute period. The reaction mixture is maintained at 50° C. for two hours at which point the NCO content is 8.56%. The reaction mixture is then cooled and the pale yellow clear solution is stored under a nitrogen blanket. The product at this point is a urethane containing a free isocyanate group. 470 grams of this reaction product are added to 200 grams of styrene, 83.43 grams of THEIC and 0.41 gram of tin octoate and the mixture charged to a one-liter flask and heated to 90° C. The reaction mixture is maintained at a temperature from 80° C. to 90° C. for about six hours at which point the NCO content is essentially zero. The resulting product is an ethylenically unsaturated isocyanurate dissolved in equal parts of styrene and is clear and almost water white. The solution has a viscosity of 278 centipoises at room temperature. 600 grams of this solution are mixed with 6 grams of cobalt naphthenate and 12 grams of Lupersol DDM and used to prepare the castings. The properties of the castings were tested and found to have the physical properties indicated in following Table I.

EXAMPLE 3

370.34 grams of Mondur MR, 245.66 grams of styrene, and 0.42 gram of hydroquinone are added to the one-liter flask as described in Example 2. 234 grams of hydroxyethylmethacrylate are then added from a dropping funnel over a 30-minute period. The mixture is then heated to 75° C. and held at that temperature for one hour at which point the percent free NCO had dropped to 4.58%. 280.8 grams of the resulting solution are mixed with 0.22 gram of tin octoate, 30 grams of THEIC, and 100 grams of styrene in a one-liter flask at 75° C. The reaction is continued until the NCO content is zero. After standing over night, the resulting solution is solidified. 450 grams of this solidified solution were then added to 50 grams of hydroxyethylmethacrylate and 50 grams of styrene to break up the strong thixotrope. The resulting solution is amber and clear and has a viscosity of 829 centipoises at room temperature. 50 grams of this solution are mixed with 0.25 gram of cobalt naphthenate, 0.5 gram of Lupersol DDM, and 0.1 gram of a 10% solution of tertiary butylcatechol in styrene. The solution gelled within two hours and had a peak exotherm of about 130° C. A casting is prepared from 300 grams of the resin solution, 1.5 grams cobalt naphthenate, 3 grams of Lupersol DDM, and 0.3 gram of 10% tertiarybutyl catechol solution in styrene. The properties of the resulting casting are shown in following Table I.

EXAMPLE 4

This example shows the preparation of an unsaturated isocyanurate from THEIC, TDI and the methacrylic acid monoester of polyoxypropylene(2)tetrabromobisphenol A.

In the first step, 148.6 grams styrene, 0.25 gram hydroquinone, and 276.8 grams of the methacrylic acid monoester of polyoxypropylene(2)tetrabromobisphenol A are added to a one-liter flask as described in Example 3 and the mixture heated to 50° C. to dissolve the monoester. 70 grams of TDI are then slowly added at such a rate that the exotherm does not exceed 70° C. The temperature of the reaction medium is maintained at 70° C. for two hours and until the NCO content is reduced to 3.37%. The reaction mixture is then cooled to room temperature. The product is a styrene solution of an isocyanate terminated prepolymer and has a viscosity of 644 centipoises at room temperature.

In a second step, 421.2 grams of the reaction product of step 1 are added to a one-liter flask along with 198.9 grams of styrene, 0.32 grams of hydroquinone, 0.32 gram of tin octoate, and 29.9 grams of THEIC. The resulting mixture is heated to 75° C. and when the NCO content has fallen to about zero, 100 grams of additional styrene are added to the viscous solution. The resulting solution has a viscosity of 690 centipoises at 25° C. and contains about 43.3% dissolved solids.

A casting is prepared from 350 grams of the solution produced in step 2 above, 7.0 grams Lupersol DDM, 3.5 grams of cobalt naphthenate, and 1.4 grams of dimethylaniline. The properties of the casting are excellent.

EXAMPLE 5

340.0 grams of TDI, 0.44 gram hydroquinone, and 254.0 grams of styrene are charged to a one-liter flask fitted as described in Example 2. 293.0 grams of hydroxypropylmethacrylate are slowly added at a rate that the exotherm does not exceed 50° C. The reaction temperature is maintained at 50° C. for two hours at which time the NCO content is 8.03%. 480.5 grams of this product are added to a one-liter reaction flask. 272.3 grams styrene, 0.4 gram hydroquinone, and 0.41 gram tin octoate are added to the flask. 80.0 grams of THEIC are then added with stirring and the resulting mixture heated to 85.5° C. The reaction mixture is maintained at a temperature between 75° C. and 80° C. for four hours at which point the NCO content is 0.28%. The resulting clear solution is quenched with 10.0 grams of hydroxyethylmethacrylate and held at 75° C. to 80° C. for an additional hour. The reaction product is then cooled and filtered. 0.35 gram of unreacted THEIC are recovered from the filter. The resulting 50% solution of vinylisocyanurate is an almost water white liquid and has a viscosity at 25° C. of 434 centipoises. A casting is prepared from this solution by mixing 350 grams of the resin solution, 5.6 grams Lupersol DDM, 2.8 grams cobalt naphthenate, and 1.4 grams tertiarybutylcatechol as a 10% solution in styrene. The properties of the casting are shown in following Table I.

EXAMPLE 6

To a one-liter, three-neck flask fitted as described in Example 2 are charged with 99.23 grams of hydroxypropyl methacrylate, 110.23 grams of methylmethacrylate, 0.18 gram of hydroquinone and 0.18 gram of dibutyltindilaurate. The mixture is heated to 60° C. and 107.73 grams of 4,4'-diisocyanate dicyclohexylmethane are added over a 30-minute period. The temperature is then raised to 80° C. and kept at this temperature for four hours. At this point the NCO content is 6.82% and the solution is cooled to room temperature. 353.6 grams of this product are added to a one-liter reaction flask to which are added 191.4 grams of methylmethacrylate, 50.0 grams of THEIC, and 0.29 gram of hydroquinone. The resulting mixture is heated to 90° C. and held at that temperature for three hours. At this point the resulting NCO content is 0.25%. The residual NCO content is then quenched by the addition of 5.7 grams of hydroxyethylmethacrylate. The final product is a water white clear solution with a viscosity of 128 centipoises at 25° C. A casting is prepared from a mixture of 350.0 grams of this solution, 7.0 grams ATC paste (50% solution of benzoyl peroxide in tricresyl phosphate), and 1.4 grams dimethylaniline. The physical properties of this casting are shown in following Table I.

TABLE I

| Example No. | Flexural Strength, psi | Tensile Strength, psi | Elongation % | HDT °C. | Charpy Impact |
|---|---|---|---|---|---|
| 1 | 24,300 | 14,300 | 3.59 | 111 | 9.56 |
| 2 | 20,500 | 11,300 | 2.65 | 111 | 6.83 |
| 3 | 22,100 | 11,500 | 2.67 | 114 | 8.25 |
| 5 | 22,000 | 12,400 | 2.56 | 118 | 7.57 |
| 6 | 22,400 | 12,500 | 3.59 | — | 8.50 |

EXAMPLE 7

To a one-liter reaction flask fitted as described in Example 2 are added 301 grams of Desmodur N-100, a triisocyanate having the formula

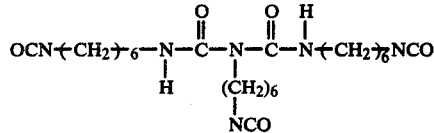

195.0 grams styrene, and 1.34 grams of hydroquinone. The mixture is then heated to 50° C. and 193.0 grams of hydroxypropylmethacrylate are added. The reaction mixture is maintained at about 60° C. for four hours at which point the NCO content is 2.93%. 536.0 grams of the resulting product are added to a one-liter reaction flask and 239.0 grams of styrene, 25.0 grams of THEIC, 0.4 gram hydroquinone and 0.4 grams stannous octoate are added. The resulting mixture is then heated to 85° C. for three hours. The reaction is complete at this point as shown by the disappearance of the NCO peaks by infrared. The product is filtered and the filtrate is used to make a casting by mixing 300 grams of the solution with 4.8 grams of Lupersol DDM and 2.4 grams cobalt naphthenate. The casting resulted in a clear, tough plastic.

EXAMPLE 8

409.0 grams of the filtrate produced in step 1 of Example 7 are charged to a one-liter flask at room temperature together with 239.0 grams of alphamethyl styrene, 70.0 grams of THEIC, 0.36 gram of hydroquinone, and 0.36 gram tin octoate. The mixture is heated to 90° C. for three hours and an NCO content of essentially zero.

The resulting colorless solution has a viscosity of 5980 centipoises at 25° C.

EXAMPLE 9

920 grams of a 50% solution of vinylisocyanurate prepared according to the procedure of Example 5, 11.04 grams of Lupersol DDM, 3.68 grams of t-butylcatechol are blended together and used to prepare a two-ply laminate with 260 grams of chopped mat and 18 grams of C-glass surfacing veil. The laminate is easy to de-air and has excellent wet out. The laminate shows no signs of warpage. The laminate is cured for twenty-four hours at room temperature and four hours at 100° C. The laminate contains 26.61% by weight of glass and has the following properties: flexural strength 16,600 psi, flexural modulus $0.88 \times 10^6$ psi, Barcol hardness 44–54, tensile strength 13,900 psi, tensile modulus $1.28 \times 10^6$ psi, and 1.24% elongation.

Although the process of this invention has been described with reference to specific reaction conditions and reactants, it will be apparent that still other different and equivalent reactants and process conditions may be substituted for those specifically described, all within the sphere and scope of this invention.

Having described the invention, what is claimed and desired to be secured by Letters Patent is:

1. A process for preparing an ethylenically unsaturated isocyanurate which comprises a first step of reacting an aromatic polyisocyanate with a monohydric alcohol containing a vinylidene group and which is selected from the group consisting of hydroxypropyl methacrylate, hydroxypropyl acrylate, hydroxyethyl methacrylate, hydroxyethyl acrylate, or mixtures thereof, to form a monoisocyanate-containing urethane, and a second step of reacting the monoisocyanate-containing urethane with tris(2-hydroxyethyl)isocyanurate to form an ethylenically unsaturated isocyanurate.

2. A process of claim 1 wherein the reaction in the first step and the reaction in the second step are conducted in the presence of a solvent which is unreactive with isocyanate groups and which contains a vinylidene group.

3. A process of claim 1 wherein the aromatic isocyanate is tolylene diisocyanate or diphenyl methane polyisocyanate.

4. A process of claim 1 which comprises (a) preparing a solution of a monohydric alcohol containing a vinylidene group and an inhibitor of vinyl polymerization in a solvent which is unreactive with isocyanate groups, (b) slowly adding an organic polyisocyanate to the solution to furnish an NCO/OH ratio of about 2 and in the presence of sufficient oxygen to keep the inhibitor active and while maintaining the temperature of the solution from about 40° C. to about 85° C. to form a monoisocyanate-containing urethane, (c) adding about one mol of tris(2-hydroxyethyl)isocyanurate to about three mols of the monoisocyanate-containing urethane and maintaining the temperature at from 60° C. to 110° C. to form an ethylenically unsaturated isocyanurate.

5. A process of claim 4 wherein the organic isocyanate is an aromatic isocyanate and the monohydric alcohol is hydroxypropylmethacrylate, hydroxypropylacrylate, hydroxyethylmethacrylate, hydroxyethylacrylate, or mixtures thereof.

6. A process of claim 5 wherein the isocyanate is tolylene diisocyanate.

7. A process of claim 4 wherein the solvent is a vinylidene monomer.

8. A process of claim 4 wherein the solvent is selected from the group consisting of styrene, methylmethacrylate, divinylbenzene, ethylmethacrylate, ethylacrylate, and mixtures thereof.

9. A process of claim 4 wherein the ratio of the combined weight of monohydric alcohol and polyisocyanate to weight of solvent used in the formation of the isocyanate-containing urethane is from about 0.33 to about 9.00 and the weight ratio of the combined weight of monoisocyanate-containing urethane and tris(2-hydroxyethyl)isocyanurate to solvent used is from about 0.33 to about 2.33.

10. An ethylenically unsaturated isocyanurate characterized by the formula;

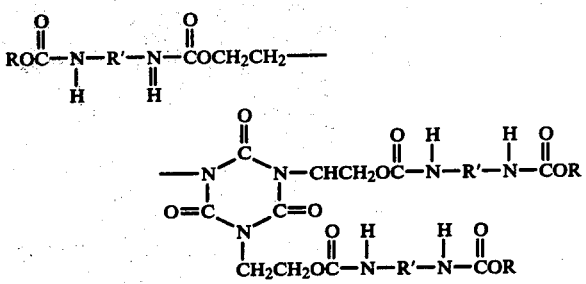

wherein R is a monovalent radical obtained by removing the hydroxyl group from the hydroxypropyl methacrylate, hydroxyethyl methacrylate, hydroxyethyl acrylate or hydroxypropyl acrylate and R' is a divalent organic radical free of a group which is reactive with an isocyanate group and is obtained by removing two isocyanate groups from an aromatic diisocyanate.

11. An ethylenically unsaturated isocyanurate of claim 10 wherein R' is tolylyl.

* * * * *